United States Patent [19]
Faust et al.

[11] Patent Number: 5,116,021
[45] Date of Patent: May 26, 1992

[54] QUICK-DISCONNECT VALVE

[75] Inventors: Valentine Faust, Bow; Dean L. Kamen, Bedford, both of N.H.

[73] Assignee: Deka Products Limited Partnership, Manchester, N.H.

[21] Appl. No.: 748,341

[22] Filed: Aug. 22, 1991

Related U.S. Application Data

[63] Continuation-in-part of Ser. No. 674,813, Mar. 22, 1991, Ser. No. 673,835, Mar. 22, 1991, abandoned, Ser. No. 674,818, Mar. 22, 1991, and Ser. No. 673,834, Mar. 22, 1991, each is a continuation-in-part of Ser. No. 615,612, Nov. 19, 1990, and Ser. No. 614,806, Nov. 19, 1990, said Ser. No. 615,612, and Ser. No. 614,806, each is a continuation-in-part of Ser. No. 523,801, May 15, 1990, and Ser. No. 345,387, May 1, 1989, Pat. No. 4,976,162, which is a continuation-in-part of Ser. No. 92,481, Sep. 3, 1987, Pat. No. 4,826,482, which is a continuation-in-part of Ser. No. 22,167, Mar. 5, 1987, Pat. No. 4,808,161, and Ser. No. 836,023, Mar. 4, 1986, Pat. No. 4,778,451.

[51] Int. Cl.⁵ .............................................. F16L 37/28
[52] U.S. Cl. .................................... 251/149.1; 251/155
[58] Field of Search ................. 251/149, 149.1, 149.3, 251/155

[56] References Cited

U.S. PATENT DOCUMENTS

| | | | |
|---|---|---|---|
| 2,299,643 | 10/1942 | Moody | 251/149.1 |
| 4,143,853 | 3/1979 | Abramson | 251/149.1 |
| 4,167,204 | 9/1979 | Zeyra | 251/149.1 X |
| 4,387,879 | 6/1983 | Tauschinski | 251/149.1 |
| 4,683,916 | 8/1987 | Raines | 251/149.1 |
| 4,915,351 | 4/1990 | Hoffman | 251/149.1 |
| 5,020,562 | 6/1991 | Richmond et al. | 251/149.1 X |

Primary Examiner—John Rivell
Attorney, Agent, or Firm—Bromberg & Sunstein

[57] ABSTRACT

A normally-closed valve that can be easily connected and disconnected. Disposed in the fluid passageway through the valve is a flexible, resilient disk and a pin mounted adjacent to the disk. The disk is mounted in a wide portion of the passageway and is held in place by the narrow portions of the passageway. The disk fits snugly into the passageway so that the edge of the disk forms a seal with the wall of the passageway. A nozzle is inserted into the passageway and urges the pin against the disk, causing the disk to deform. When the disk deforms, its effective diameter decreases, and its edge separates from the passageway wall, permitting fluid to flow through the valve. The narrow sections of the passageway wall have channels disposed therein for permitting flow when the disk is deformed. The pin also has channels on its surface to permit flow around it.

15 Claims, 4 Drawing Sheets

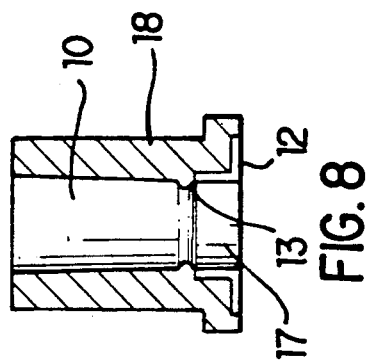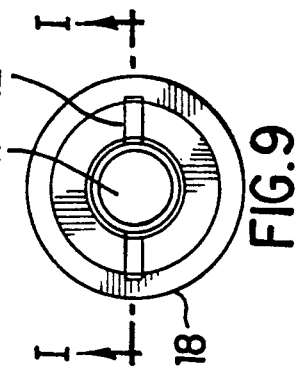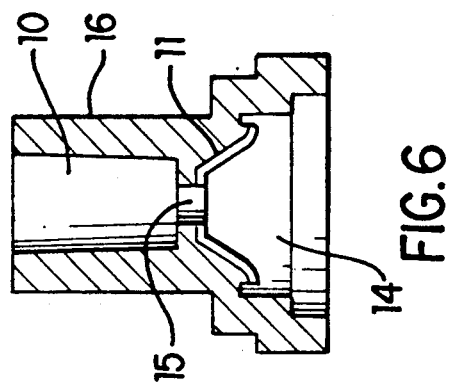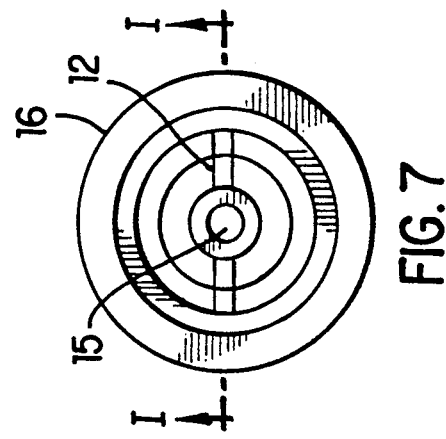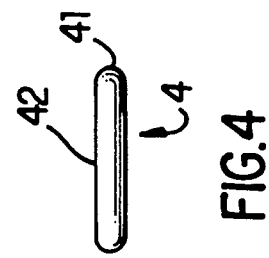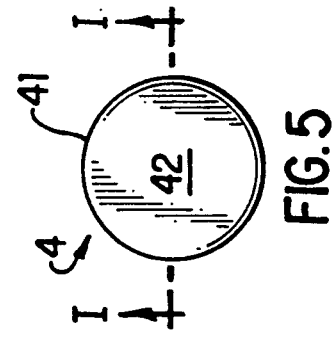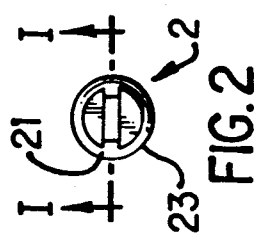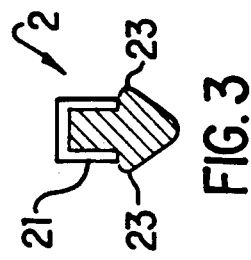

QUICK-DISCONNECT VALVE

This application is a continuation-in-part of application Ser. No. 674,813 (for Fluid-Control Valve System), application Ser. No. 673,835 (for Constant-Pressure Fluid Supply System) now abandoned, application Ser. No. 674,818 (for Fluid Management System with Auxiliary Dispensing Chamber), and application Ser. No. 673,834 (for Membrane-Based Rotary Peristaltic Pump), each of which was filed Mar. 22, 1991 and each of which is a continuation-in-part of application Ser. No. 615,612 filed Nov. 19, 1990, (for Acoustic Volume Measurement with Fluid Management Capability), and application Ser. No. 614,806 filed Nov. 19, 1990 (for Integral Intravenous Fluid Delivery Device), which are continuations-in-part of application Ser. No. 523,801 filed May 15, 1990 (for a Valve System with Removable Fluid Interface) and application Ser. No. 345,387 filed May 1, 1989, issued Dec. 11, 1990 as U.S. Pat. No. 4,976,162 (for an Enhanced Pressure Measurement Flow Control System), which is a continuation-in-part of application Ser. No. 092,481 filed Sep. 3, 1987, issued as U.S. Pat. No. 4,826,482, which is a continuation-in-part of application Ser. No. 022,167 filed Mar. 5, 1987, issued as U.S. Pat. No. 4,808,161, and application Ser. No. 836,023, filed Mar. 4, 1986, issued as U.S. Pat. No. 4,778,451. Filed concurrently herewith in an application for Constant-Pressure Fluid Supply System with Multiple Fluid Capability by Normand, Durand, Seale and Kamen application Ser. No. 748,346 filed Aug. 22, 1991. These related applications are hereby incorporated herein by reference.

TECHNICAL FIELD

The invention relates generally to valves that may be easily connected or disconnected, and more specifically to such valves employed in medical intravenous fluid delivery systems.

BACKGROUND OF THE INVENTION

U.S. Pat. No. 5,020,562 shows a check valve assembly having resilient valve elements that normally prevent flow through the valve by pressing against a valve seat, but when compressed by a fitting the top of the resilient element the top of the element moves away from the valve seat, thereby permitting fluid to flow therethrough.

U.S. Pat. Nos. 4,683,916 and 4,535,820 show one-way check valves, which use a resilient disk. When these valves are opened it is the outer portion of the disk that is displaced; the disk's central portion is not displaced.

SUMMARY OF THE INVENTION

The present invention provides a valve for permitting flow of a fluid therethrough when actuated by a nozzle, and otherwise preventing flow of fluid therethrough. The valve has a fluid passageway disposed therethrough, the passageway is bounded by a wall. The fluid passageway may have two relatively narrow sections and a relatively wide section disposed between the two narrow sections. The valve also includes a relatively flat, resilient, flexible seal member disposed transversely to the fluid passageway, preferably in the wide section of the passageway. The edge of the seal member is normally disposed against the wall of the fluid passageway so as to prevent the flow of fluid past the seal member. However, when the central portion of the seal member is urged in a direction generally parallel to the fluid passageway, the central portion is displaced with respect to the edge and with respect to the valve housing, and the seal member deforms so as to cause the edge of the seal member away from the wall. This deformation allows the fluid to flow through the passageway by passing between the wall and the seal member. The valve may include a device, preferably a pin, responsive to actuation by the nozzle, for urging the central portion of the seal member in a direction generally parallel to the fluid passageway so as to deform the seal member in the manner described above. Channels may be disposed in the wall of the fluid passageway between the first narrow section and the wide section, and between the wide section and the second narrow section, so as to permit flow through the channels when the seal member is deformed by the urging member. The pin may also have a channel disposed on the surface thereof so as to permit flow past the pin, when the pin is pressed against the seal member by the nozzle. In order to prevent the pin from falling out of the passageway when the nozzle is removed, the wall in its first narrow section may have a lip disposed thereon, and the pin may have a shoulder disposed thereon with the pin's shoulder located between the wall's lip and the seal member.

The valve, when closed, prevents flow therethrough because the edge of the seal member seals against the wall of the passageway. By deforming the seal member, its effective diameter decreases, and its edge moves away from the wall. Thus fluid is able to flow between the wall and the seal member. The transition between the wide section and the second narrow section of the passageway serves to obstruct the movement of the edge of the sealing member with respect to the passageway wall in a direction parallel to the passageway, as the central portion of the seal member is being urged in said parallel direction and the edge is moving away from the passageway wall. The channels in the passageway wall allow fluid to pass around the seal member, even though the seal member in its deformed shape may be urged against other portions of the wall.

BRIEF DESCRIPTION OF THE DRAWINGS

FIG. 2 is an top plan view of the pin of the valve shown in FIG. 1.

FIG. 3 is a cross-sectional view of the pin shown in FIG. 2.

FIG. 4 is a side view of the seal member of the valve shown in FIG. 1.

FIG. 5 is a top view of the seal member shown in FIG. 4.

FIG. 6 is a cross-sectional view of the bottom half of the valve housing shown in FIG. 1.

FIG. 7 is a top view of the bottom half of the valve housing shown in FIG. 1.

FIG. 8 is a cross-sectional view of the top half of the valve housing shown in FIG. 1.

FIG. 9 is a bottom view of the portion of the valve housing shown in FIG. 8.

DESCRIPTION OF SPECIFIC EMBODIMENTS

Figure 1:
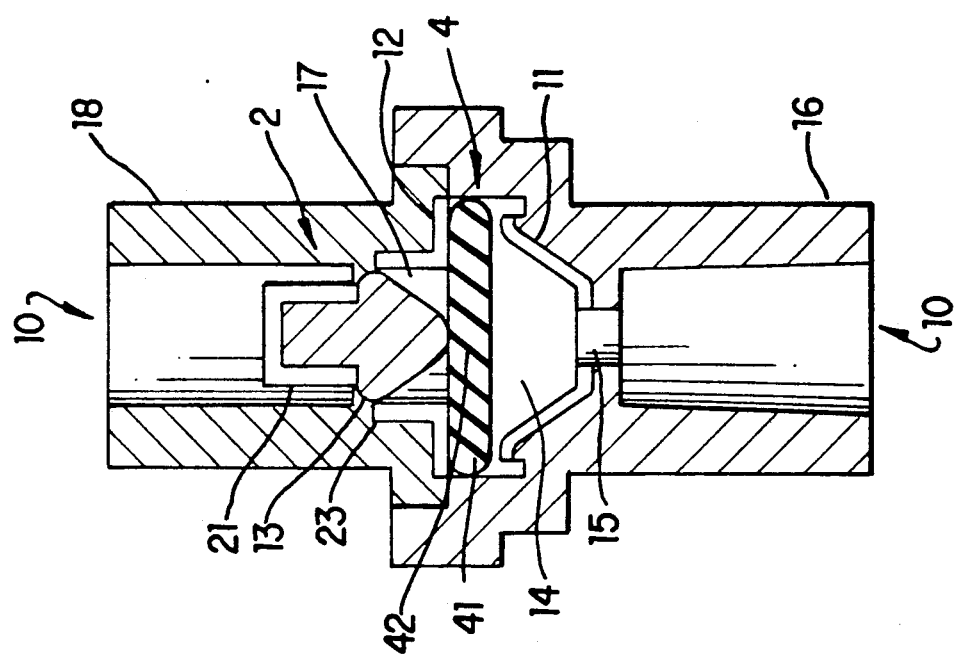
FIG. 1 is a cross-sectional view of a preferred embodiment of the invention.

The valve shown in FIG. 1 has a fluid passageway 10, the wall of which is formed by two parts, 16 and 18, making up the valve housing. The lower part 16 of the valve housing may be in fluid communication with an intravenous line. The passageway has relatively narrow sections, 15 and 17, and a relatively wide section 14. Disposed in the passageway 10 are a pin 2 and a flexible, resilient, fluidimpermeable disk 4, the pin 2 being located in a narrow section 17 and the disk 4 being located in the wide section 14 of the passageway 10. The disk 4 fits snugly in the wide section 14, so that a seal is formed between the disk's edge 41 and the wall 16 of the passageway 10. The disk 4 and the passageway's wide section 14 are located between the passageway's two narrow sections, 15 and 17. The narrow sections obstruct the movement of the disk 4 up and down the passageway 10; the disk's edge 41 is especially obstructed by the narrow sections. Adjacent to the disk's central portion 42 is the pin 2. Channels 11 and 12, are disposed in the wall of the passageway 10 between the narrow sections, 15 and 17, and the wide section 14. Channels 21 are also disposed along the sides and the top of the pin 2. The pin 2 also has a shoulder 23 that works with a lip 13 on the passageway wall to prevent the pin 2 from falling out of the passageway 10. FIGS. 2-9 show additional views of the separate components making up the valve shown in FIG. 1.

Figure 11:
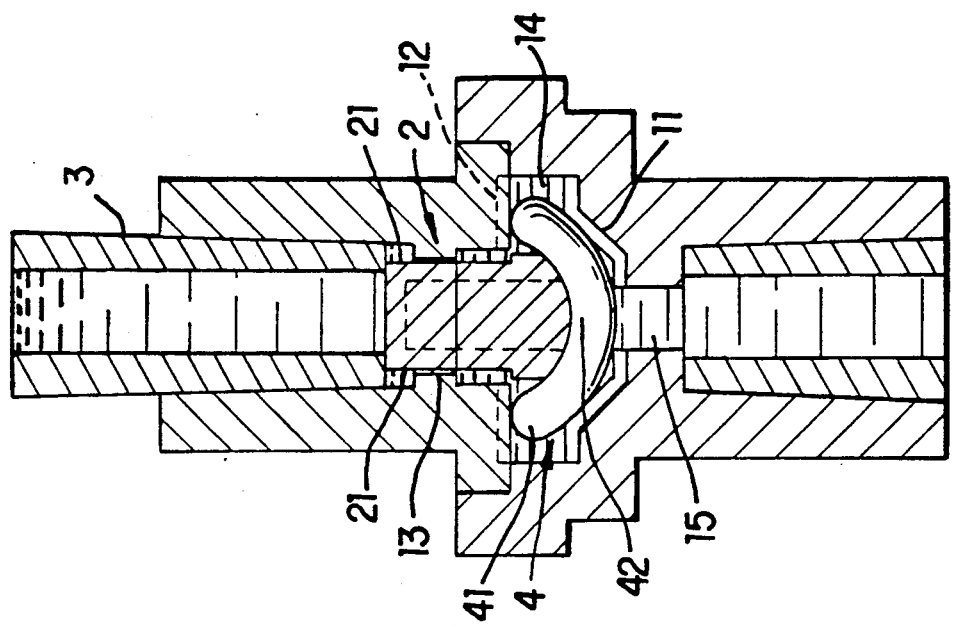
FIG. 11 is a cross-sectional view of the valve shown in FIG. 10 in an open position.
Figure 10:
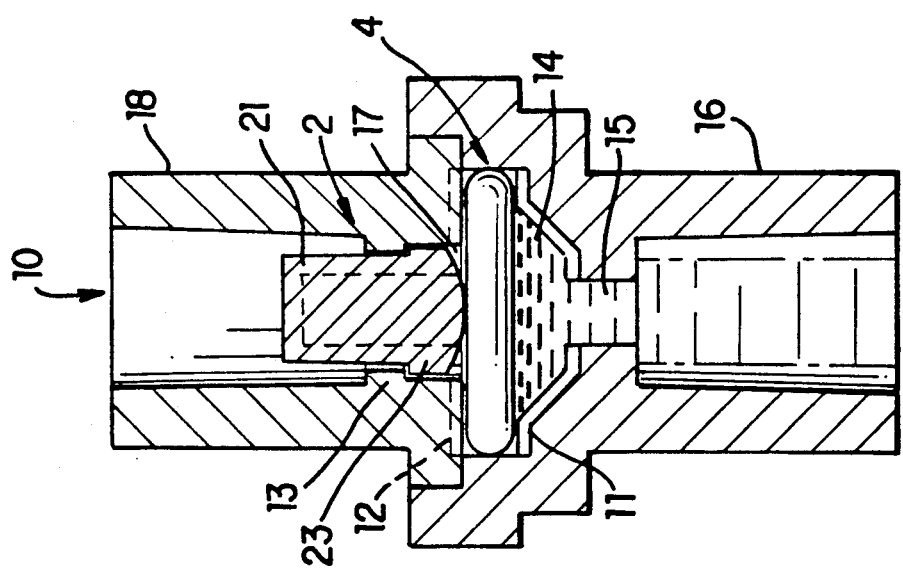
FIG. 10 is a cross-sectional view of an alternative embodiment of the invention in a closed position.
Figure 16:
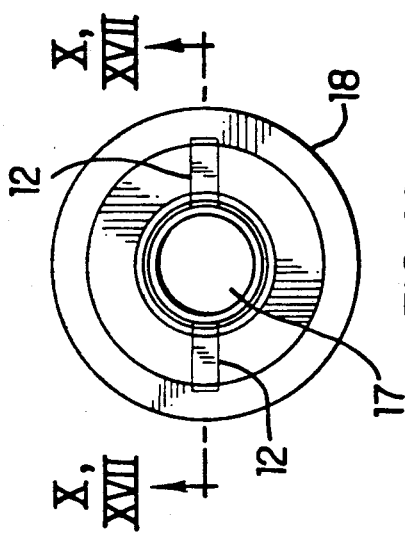
FIG. 16 is a bottom view of the top half of the valve housing shown in FIGS. 10 and 11.
Figure 17:
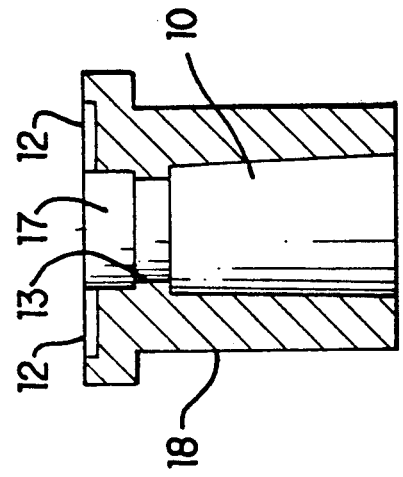
FIG. 17 is a cross-sectional view of the valve housing shown in FIG. 16.
Figure 14:
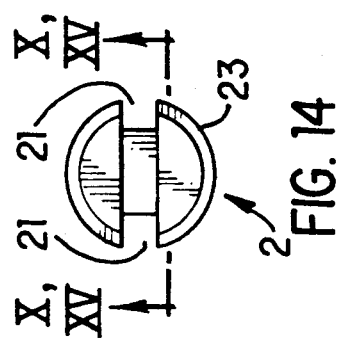
FIG. 14 is a top view of the pin of the valve shown in FIGS. 10 and 11.
Figure 15:
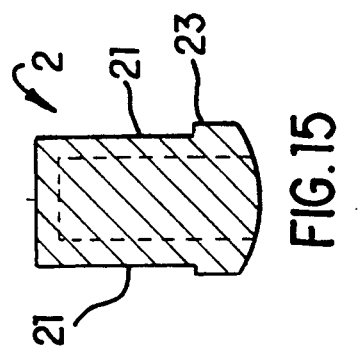
FIG. 15 is a cross-sectional view of the pin shown in FIG. 14.
Figure 12:
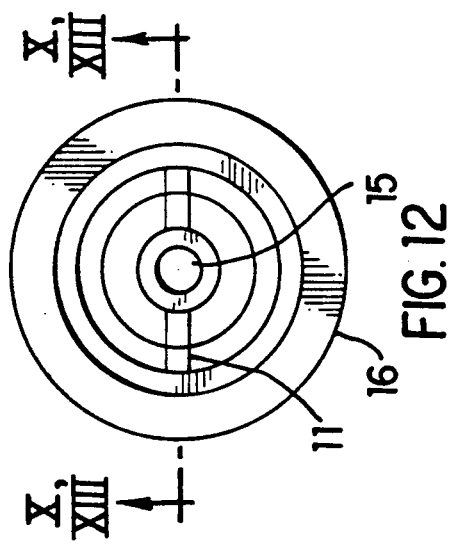
FIG. 12 is a top view of the bottom half of the valve housing shown in FIGS. 10 and 11.
Figure 13:
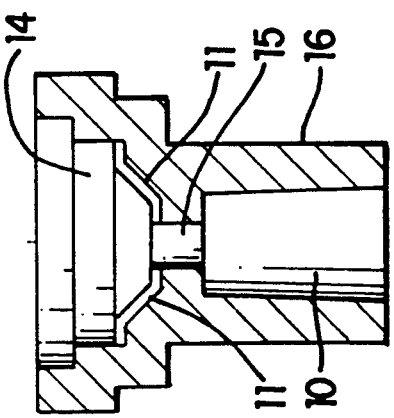
FIG. 13 is a cross-sectional view of the portion of the valve housing shown in FIG. 12.

The valve shown in FIG. 10 has the same basic configuration of components as the valve shown in FIG. 1, but, as will be discussed below in greater detail, the shape of the pin 2 and the passageway 10 are different. Additional views of some of the components of the FIG. 10 valve are shown in FIGS. 12-17. The stippling in FIG. 10 shows the presence of fluid; the lower portion of the valve is occupied by a fluid, which may be in communication with a main intravenous line. FIG. 11 shows the valve opened by the nozzle 3 of a syringe or a fitting for a secondary intravenous line. As in FIG. 10, the stippling in FIG. 11 indicates the presence of fluid; there is fluid throughout the passageway 10 of the valve shown in FIG. 11. The nozzle 3 has urged the pin 2 downward; the pin 2 in turn urges the disk's central portion 42 downward. The disk's edge 41 does not move downward because it is obstructed by the wall of the passageway's second narrow section 15. As a result, the disk 4 is deformed, and its effective diameter reduced. This causes the disk's edge 41 to separate from the wall of the passageway's wide portion 14, thereby breaking the seal between the disk 4 and the wall that existed when the valve was closed, as in FIG. 10. When the disk 4 is deformed, its effective thickness is increased. This increase in effective thickness could block flow through the valve if it did not have channels, but the fluid may flow through the channels, 11 and 12, in the passageway's wall. Channels 21 in the pin 2 allow fluid to flow out of the nozzle 3 and past the pin 2 and the lips 13 disposed on the passageway's wall. Once the nozzle 3 opens the valve fluid may flow in either direction—either out of or into the nozzle 3. Such a feature is advantageous, since it allows fluid to be either added to or removed from the main intravenous line.

In the valve shown in FIG. 1 the wall's channels 12 extend further up the passageway 10, and the pin's channels 21 do not extend as far down, as the corresponding channels in the FIG. 10 valve. The FIG. 1 valve has an additional sealing point, between the pin's shoulders 23 and the wall's lips 13, whereas the FIG. 10 valve has only the sealing point between the disk's edge 41 and the wall of the passageway's wide section 14. When the FIG. 10 valve is closed, fluid above the disk 4 is exposed to the atmosphere and therefore subject to contamination. Because the pin's channels 21 are quite narrow (and even if they are made as wide as possible), it is more difficult to flush away all the fluid above the disk 4. When the FIG. 1 valve is closed, only the fluid above the lip-shoulder 13-23 seal is exposed to atmosphere and therefore subject to contamination. This exposed fluid, since there is less of it and it is more exposed, may be more easily flushed (or even wiped away) than the exposed fluid of the FIG. 10 valve.

In another embodiment of the invention, the pin may be mounted to the tip of the nozzle, instead of being mounted within the valve. Such an embodiment is not as preferable as the those shown in FIGS. 1 and 10, since it requires the use of a specially constructed nozzle. The embodiments shown in FIGS. 1 and 10 may be sized so that they can accept the nozzles of standard syringes and fittings.

What is claimed is:

1. A valve for permitting flow of a fluid therethrough when actuated by a nozzle, and otherwise preventing flow of fluid therethrough, the valve comprising:

a fluid passageway bounded by a wall; and a relatively flat resilient seal member having an edge and a central portion, the seal member being disposed transversely to the fluid passageway such that the edge of the seal is normally disposed against the wall of the fluid passageway so as to prevent the flow of fluid past the seal member, and such that, when the central portion of the seal member is urged in a direction generally parallel to the fluid passageway, the seal member deforms such that the central portion is displaced and such that the edge of the seal member separates from the wall so that fluid may flow through the passageway by passing between the wall and the seal member.

2. A valve according to claim 1 further including means, responsive to actuation by the nozzle, for urging the central portion of the seal member in a direction generally parallel to the fluid passageway so as to deform the seal member and to cause the edge of the seal member away from the wall such that fluid may flow through the passageway.

3. A valve according to claim 2, wherein the central portion of the seal member has a first face and a second face, and wherein the urging means includes a pin disposed in the fluid passageway adjacent to the first face of the seal member, such that, when the pin is pressed by the nozzle, the pin urges the central portion of the seal member in a direction generally parallel to the passageway.

4. A valve according to claim 3, wherein the fluid passageway has a first narrow section, a second narrow section and a wide section disposed between the two narrow sections, and wherein the seal member is disposed in the wide section.

5. A valve according claim 4, wherein a first channel is disposed in the wall of the fluid passageway between the first narrow section and the wide section, and a second channel is disposed in the wall between the wide section and the second narrow section, so as to permit flow through the channels when the seal member is deformed by the pin.

6. A valve according to claim 5, wherein the pin has a channel disposed on the surface thereof so as to permit flow past the pin, when the pin is pressed against the seal member by the nozzle.

7. A valve according to claim 6, wherein the wall in first narrow section has a lip disposed thereon, and wherein the pin has a shoulder disposed thereon, such that the lip keeps the pin within the passageway.

8. A valve according to claim 1, further including means for obstructing the movement of the edge of the sealing member with respect to the passageway wall in a direction parallel to the passageway, as the central portion of the seal member is being urged in said parallel direction and the edge is moving away from the passageway wall.

9. A valve according to claim 2, further including means for obstructing the movement of the edge of the sealing member with respect to the passageway wall in a direction parallel to the passageway, as the central portion of the seal member is being urged in said parallel direction and the edge is moving away from the passageway wall.

10. A valve according to claim 3, further including means for obstructing the movement of the edge of the sealing member with respect to the passageway wall in a direction parallel to the passageway, as the central portion of the seal member is being urged in said parallel direction and the edge is moving away from the passageway wall.

11. A valve according to claim 10, wherein the pin has a channel disposed on the surface thereof so as to permit flow past the pin, when the pin is pressed against the seal member by the nozzle.

12. A valve according claim 11, further including means, disposed in the obstruction means, for permitting flow through the obstruction means when the seal member is deformed by the pin.

13. A valve according to claim 12, wherein the means for permitting flow includes a channel.

14. A valve according claim 8, further including means, disposed in the obstruction means, for permitting flow through the obstruction means when the seal member is deformed by the pin.

15. A valve according to claim 14, wherein the means for permitting flow includes a channel.

* * * * *